United States Patent [19]

Jauw

[11] Patent Number: 5,178,853
[45] Date of Patent: Jan. 12, 1993

[54] PACKAGED OPHTHALMIC PREPARATION COMPRISING A POVIDONE-IODINE SOLUTION

[75] Inventor: Tjoe H. Jauw, Amsterdam, Netherlands

[73] Assignee: Dagra Pharma B.V., Verrijn Stuartweg, Netherlands

[21] Appl. No.: 759,586

[22] Filed: Sep. 16, 1991

[30] Foreign Application Priority Data

Sep. 18, 1990 [NL] Netherlands ............ 9002049

[51] Int. Cl.$^5$ .............................................. A61K 31/74
[52] U.S. Cl. .............................. 424/78.04; 424/78.36; 424/667
[58] Field of Search ................ 424/667, 78.04, 78.36

[56] References Cited

U.S. PATENT DOCUMENTS 4,996,048 2/1991 Bhagwat et al. ............... 424/80

OTHER PUBLICATIONS

Chemical Abst. 105:17912h (1986). Roberts et al.
Chemical Abst. 78:106019P (1973). White et al.

Primary Examiner—Frederick E. Waddell
Assistant Examiner—Zohreh A. Fay
Attorney, Agent, or Firm—Beveridge, DeGrandi & Weilacher

[57] ABSTRACT

This invention relates to an ophthalmic preparation of povidone iodine in a packaging of bottle glass type I or polyethyleneterephthalate with a dropper of polypropylene, polyethylene and/or polytetrafluoroethylene coated bromobutyl rubber.

11 Claims, No Drawings

PACKAGED OPHTHALMIC PREPARATION COMPRISING A POVIDONE-IODINE SOLUTION

The present invention relates to an ophthalmic preparation comprising a povidone-iodine solution containing 0.01 to 0.1% of available iodine in a sterile primary packaging.

Such a preparation is known from the communication in the "Pharmaceutisch Weekblad 117" page 420 (1982) by J. T. G. Jansen. Said ophthalmic preparation is used for therapeutical and profylactical treatmen of conjunctivitis (keratoconjunctivitis epidemica) caused by adenoviruses. Said preparation contains 0.03% of available iodine. The compostion is prepared by diluting a 10% povidone-iodine solution commercially available 30 times with a sterile physiological saline. The solution obtained is subsequently filtered in an aseptic laminar air-flow clean bench through a sterile 0.2 μm membrane filter into a sterile ophthalmic packaging. As ophthalmic packaging or primary packaging polyethylene flexioles are recommended. The shelf-life of the ophthalmic preparation in said primary packaging when it is stored in the refrigerator is only about 1 month. The shelf-life is that short since a rapid decrease of the concentrations of available iodine and free iodine occurs.

European patent application 0,371,283 relates to flexible plastic packagings containing a povidone iodine solution. In order to improve the stability of the povidone-iodine solution and to minimize the leaching of iodine through the packaging a quantity of additional iodide is added to the solution. It is stated that as a result of the addition the stability improves greatly when plastic materials, particularly all kinds of polyethylene, are used as packaging, while when using glass as packaging the already reasonable stability does not improve considerably. Said European patent application is silent about the material of the dropper present on the packaging, while said dropper may also form an important source for leaching of iodine. Further it appears from the examples that in spite of the addition of extra iodide there is often still a considerable decrease of the available iodine.

French patent application 2,469,357 describes a packaging consisting of a flexible, plastic bottle having a dosage cap and containing a quantity of solid elementary iodine and means to retain the iodine within the bottle. The iodine is dosed as an aqueous solution after addition of water. The bottle may consist of thermoplastic materials such as polyvinyl-chloride, polyethylene and polypropylene, preferably with a dark pigment. However, all these materials appear to be unsuitable as packaging for a povidone iodine solution, because a rapid decrease of the concentration of available iodine occurs.

Therefore, there is a need for an ophthalmic povidone-iodine preparation which has a longer shelf-life so that it can also be manufactured commercially.

The present invention provides such an ophthalmic preparation by selecting a specific primary packaging. The ophthalmic preparation according to the invention is characterized in that the primary packaging consists of a bottle of glass type I or polyethyleneterephthalate with a dropper of polypropylene, polyethylene and/or polytetrafluoroethylene coated bromobutyl rubber.

As a result thereof, the shelf-life of the ophthalmic preparation is considerably extended to 1-2 years at room temperature, depending upon the precise preparation of the ophthalmic solution.

The bottle is the most important part of the packaging in that it contacts the solution most intensively. An extensive examination showed that only the two abovementioned types of materials are suitable. Of these two materials polyethyleneterephthalate is preferred because it is a flexible, plastic material.

The dropper also may have a considerable affect on stability, depending of the contact area, the permeability to iodine and the absorption properties with respect to iodine. Apart from the material, all conventional types of droppers can be used such as a zentrop frame, screw cap with dropper, pipette frame, drop cap, etc.

When the contact area of the dropper is considerably large, polypropylene is preferred over polyethylene. Examples of suitable primary packagings according to the invention are:

a bottle of glass type I (Eur.Ph.) with a polypropylene (zentrop) dropper, a bottle of glass type I with a bromobutyl rubber dropper coated with Teflon ® (polytetrafluoroethylene), a bottle of polyethyleneterephthalate with a polyethylene (LDPE) dropper and a polypropylene screw cap.

The contents of the bottles usually varies from 5 to 15 ml, but it can also be higher.

The ophthalmic preparation according to the invention can be improved further by a proper selection of the povidone-iodine. The current 10% povidone-iodine solution is prepared on the basis of povidone-iodine K-30, which means that the used povidone has a K-value of 30 (the K-value can be determined by the method described in USP under the monography "Povidone"). Also the 10% Betadine ® solution used as starting material in the above-mentioned article of J. T. G. Jansen, contains Povidone K-30. It has been found that the concentration of free iodine of the diluted ophthalmic solution prepared therefrom amounts to about 9 ppm (9 mg/l) (Ziekenhuisfarmacia 1, pages 3 to 6, 1985). Such a high concentration of free iodine increases the risk of irritation.

It has now been found that by using povidone having a K-value of more than 30, and preferably more than 60, most preferably about 90, the concentration of free iodine is about 2 to 3 ppm. By using a povidone-iodine having a higher K-value the effectiveness of the ophthalmic preparation is maintained, whereas the occurence of irritations is minimized. The povidone-iodine usually contains 9 to 12% of iodine (available iodine) and most often about 10%.

A further improvement of the ophthalmic preparation according to the invention can be attained by adjusting the pH of the povidone-iodine solution at 5.5 to 6.5 and preferably at 5.8 to 6.2 by means of a buffer. The buffer used to adjust the pH may for example be a phosphate buffer. When no buffer is used the depreparation reaction $I_2 \rightarrow 2I$ may lead to the formation of HI, resulting in an unacceptably low pH, e.g. lower than 5. The pH should remain below 6.5, otherwise the iodine will decompose.

To the povidone-iodine solution other usual additives may be added, such as sodium chloride for obtaining an isotonic solution, and potassium iodate and potassium iodide for further stabilising the solution.

The ophthalmic preparation according to the invention can be prepared by dissolving the povidone-iodine and the other ingredients in water in the right proportions. The solution obtained is subsequently filtered through a 0.2 μm sterile filter into a sterile primary packaging as defined above. When povidone K-90 is used the filtration through an absolute 0.2 μm filter may present difficulties. Alternatively, filtration may also take place through a nominal 0.2 μm filter. Due to the disinfective effect of the iodine a suitable and safe product is obtained herewith.

The preparation contains 0.01 to 0.1%, preferably 0.02 to 0.04% and usually about 0.03% of available iodine.

The invention is further illustrated by the following examples and comparative examples.

EXAMPLE I 30.0 mg of povidone-iodine K-90 containing 10% of available iodine was dissolved into purified water together with 75.0 mg of sodium chloride, 3.3 mg of potassium iodide and 0.3 mg of potassium iodate and purified water added to a total volume of 10.0 ml. The pH was adjusted at 6.0 with sodium hydroxyde, and to maintain said pH a phosphate buffer consisting of disodium phosphate and citric acid was added. Afterwards the solution was filtered through a nominal 0.2 μm filter into a sterile primary packaging consisting of a 10 ml bottle of glass type I with a polypropylene zentrop dropper. Thus, an ophthalmic preparation was obtained which contained a povidone-iodine concentration of about 0.3% and which contained approximately 0.03% of available iodine. The concentration of free iodine was about 2 ppm. The obtained ophthalmic preparation remained stable when it was stored during at least two years at room temperature.

EXAMPLE II

The procedure of Example I was followed, except that the dropper consisted of a bromobutyl rubber dropper coated with Teflon ®. After 12 months the quantity of available iodine was 6% of the declared initial value. After 18 months this percentage reduced to 83%.

EXAMPLE III

The procedure of Example I was followed, except that the primary packaging consisted of a polyethyleneterephthalate bottle of 10 ml with a polyethylene dropper and a polypropylene screw cap. After 24 months the quantity of available iodine was still about 90% of the declared initial value.

COMPARATIVE EXAMPLE 1

The procedure of Example I was followed, except that the primary packaging consisted of a pvc bottle. After 12 months the quantity of available iodine was about 90% of the declared initial value. After 24 months this percentage reduced to approximately 80%.

COMPARATIVE EXAMPLE 2

The procedure of Example I was followed, except that povidone iodine K-30 was used and the primary packaging consisted of a pvc bottle. After 12 months the quantity of available iodine was approximately 60% of the declared value.

COMPARATIVE EXAMPLE 3

The procedure of Example II was followed, except that the drop casing consisted of bromobutyl rubber without a coating. After two weeks the quantity of available iodine was about 30% of the declared initial value.

COMPARATIVE EXAMPLE 4

The procedure of the Example I was followed, except that the primary packaging consisted of a polyethylene flexiole with a polypropylene screw cap. After two weeks the quantity of available iodine was about 50% of the declared initial value.

I claim:

1. A packaged ophthalmic preparation having an extended shelf life comprising a povidone-iodine solution containing 0.01 to 0.1% of available iodine in a sterile primary packaging, wherein said primary packaging consists of a bottle of glass type I or polyethyleneterephthalate with a dropper of polypropylene, polyethylene and/or polytetrafluoroethylene coated bromobutyl rubber.

2. An ophthalmic preparation according to claim 1, characterized in that the primary packaging consists of a bottle of glass type I with a zentrop dropper of polypropylene or polytetrafluoroethylene coated bromobutyl rubber.

3. An ophthalmic preparation according to claim 1, characterized in that the primary packaging consists of a bottle of polyethyleneterephthalate with a polyethylene dropper and a polypropylene screw cap.

4. An ophthalmic preparation according to claim 1, characterized in that the povidone-iodine solution is prepared from povidone having a K-value of more than 30.

5. An ophthalmic preparation according to claim 4, characterized in that the povidone-iodine solution is prepared from povidone having a K-value of more than 60.

6. An ophthalmic preparation according to claim 5, characterized in that the povidone-iodine solution is prepared from povidone having a K-value of more than 90.

7. An ophthalmic preparation according to claim 4 obtained by filtering the povidone-iodine solution through a nominal 0.2 μm filter into the sterile primary packaging.

8. An ophthalmic preparation according to claim 1, characterized in that the pH of the povidone-iodine solution is adjusted at 5.5 to 6.5 by means of a buffer.

9. An ophthalmic compostion according to claim 1, characterized in that the povidone-iodine solution contains 0.02 to 0.04% of available iodine.

10. An ophthalmic preparation according to claim 6 obtained by filtering the povidone-iodine solution through a nominal 0.2 μm filter into the sterile primary packaging.

11. A method of extending the shelf life of povidone-iodine solutions, said method consisting essentially of filtering a povidone-iodine solution containing 0.01 to 0.1% of available iodine into a sterile primary packaging, wherein said primary packaging consists of a bottle of glass type I or polyethyleneterephthalate with a dropper of polypropylene, polyethylene and/or polytetrafluoroethylene coated bromobutyl rubber.

* * * * *